(12) United States Patent
Roger

(10) Patent No.: US 7,427,283 B2
(45) Date of Patent: Sep. 23, 2008

(54) SURGICAL FIXATION DEVICE

(75) Inventor: Gregory James Roger, Crows Nest (AU)

(73) Assignee: Australiam Surgical Design & Manufacturing Pty Ltd, New South Wales (AU)

( * ) Notice: Subject to any disclaimer, the term of this patent is extended or adjusted under 35 U.S.C. 154(b) by 356 days.

(21) Appl. No.: 10/482,921

(22) PCT Filed: Jul. 10, 2002

(86) PCT No.: PCT/AU02/00949

§ 371 (c)(1),
(2), (4) Date: Mar. 18, 2004

(87) PCT Pub. No.: WO03/005915

PCT Pub. Date: Jan. 23, 2003

(65) Prior Publication Data

US 2004/0153075 A1  Aug. 5, 2004

(30) Foreign Application Priority Data

Jul. 10, 2001  (AU) ........................... PR6264

(51) Int. Cl.
*A61B 17/56* (2006.01)

(52) U.S. Cl. .................... 606/72; 606/92; 606/78; 606/215

(58) Field of Classification Search ........... 606/60, 606/69, 70, 71, 72, 73, 74, 76, 77, 78, 86, 606/213, 214, 215, 92, 93, 94
See application file for complete search history.

(56) References Cited

U.S. PATENT DOCUMENTS

| | | | | | |
|---|---|---|---|---|---|
| 3,223,083 | A | * | 12/1965 | Cobey | 606/92 |
| 3,805,776 | A | * | 4/1974 | Thiele | 606/60 |
| 3,828,772 | A | * | 8/1974 | Thiele | 606/60 |
| 3,835,538 | A | * | 9/1974 | Northcutt | 433/9 |
| 4,872,840 | A | * | 10/1989 | Bori | 433/173 |
| 5,370,662 | A | * | 12/1994 | Stone et al. | 606/232 |
| 5,683,419 | A | * | 11/1997 | Thal | 606/232 |
| 5,941,911 | A | | 8/1999 | Buechel | 623/16 |
| 6,554,852 | B1 | * | 4/2003 | Oberlander | 606/232 |
| 6,565,572 | B2 | * | 5/2003 | Chappius | 606/73 |
| 6,620,185 | B1 | * | 9/2003 | Harvie et al. | 606/232 |

OTHER PUBLICATIONS

Persing et al, J NEUROSURG 66, 1987, pp. 793-799, Late surgical treatment of unilateral coronal synostosis using methyl . . . .

Replogle et al, NEUROSURGERY, vol. 39, No. 4, Oct. 1996, pp. 747-749, Acrylic Cranioplasty Using Miniplate Struts.

Sherburn et al, Surg Neurol 46, 1996, pp. 292-294, A New Method of Acrylic Cranioplasty.

* cited by examiner

*Primary Examiner*—Eduardo C. Robert
*Assistant Examiner*—James L Swiger
(74) *Attorney, Agent, or Firm*—Jacobson Holman PLLC

(57) ABSTRACT

A bone anchoring device, the device including a body having a first end affixable with a bone; and an engagement device engageable with a settable compound brought into contact with the engagement device prior to setting of the settable compound.

20 Claims, 5 Drawing Sheets (a)  (b)  (c)  (d)

SURGICAL FIXATION DEVICE

This is a nationalization of PCT/AU02/00949 filed Jul. 10, 2002 and published in English.

FIELD OF THE INVENTION

The present invention relates to a device and method for providing fixation for fractures in bone.

BACKGROUND OF THE INVENTION

Fixation of traditional cranio-facial fractures in fracture fixation and reconstructive surgery has often involved the use of titanium plates bent by surgeons to the contour of the bone and then secured to the bone by titanium screws. Although biocompatible, the titanium screws and plates often cause complications such as bone resorption due to stress shielding of the bone, bone necrosis and can loosen, requiring removal of the hardware.

Bio-resorbable plates and screws have also been used in cranio-facial surgery. The bio-resorable plates also require bending by the surgeon intra-operatively, to conform with the geometry of the subject's cranium.

In the use of titanium and bio-resorbable plates there exists a risk of the plates gradually returning toward their original shape due to residual stresses causes from bending by the surgeon.

Another complication in existing surgical hardware is often the holes in the plates are either too near or to far from the fracture site, and adequate fixation is not achieved.

SUMMARY OF THE INVENTION

In a first aspect, the present invention is a bone anchoring device, the device comprising:
 a body having:
 a first end affixable with a bone; and
 an engagement means engageable with a settable compound brought into contact with the engagement means prior to setting of the settable compound.

In a second aspect, the present invention is a bone anchoring device, the device comprising:
 a body having:
 a first end affixable with a bone; and
 an engagement means engageable with a settable compound and engageable with a linking resorbable or permanent linking thread, suture or wire, brought into contact with the engagement means prior to setting of the settable compound.

In a third aspect, the present invention is a kit when used in bone fixation, the kit comprising:
 a first bone anchoring device;
 at least a second bone anchoring device; and
 a settable compound adapted, on setting in use for bone fixation, to extend between and engage with the bone anchoring devices.

In one embodiment, the kit has a first and a second bone anchoring device.

In a further embodiment, the kit has a first, a second and at least a third bone anchoring device. In one embodiment, the settable compound can extend from the first to the second bone anchoring device and from the second to the third bone anchoring device. In a further embodiment, the settable compound extends first to the second bone anchoring device, from the second to the third bone anchoring device and from the third to the first bone anchoring device.

In a fourth aspect, the present invention is a method of bone fixation, the method including the steps of:
 (i) affixing a first bone anchoring device to a bone;
 (ii) affixing at least a second bone anchoring device to the bone;
 (iii) applying a settable compound such that the settable compound conforms substantially to the geometry of the surface of the bone, the settable compound extending from the first bone anchoring device to the at least a second bone anchoring device, such that upon setting, the settable compound engages with the bone anchoring devices.

In one embodiment of the above aspects, the bone anchoring means has a second end proximal the first end.

In a further embodiment of the above aspects, the engagement means is positioned at or adjacent the second end. Examples of engagement means can include a cusp, flange, contour, lip, pedestal, coupling or boss.

In another embodiment of the above aspects, the bone anchoring device can be made from a biocompatible material. Example of biocompatible materials include titanium, titanium alloy, stainless steel, cobalt chrome, polymethylmethacrylate, PEEK, polytetraflouroethylene, polyvinylchloride, alumina and zirconia In yet another embodiment of the above aspects, the anchoring device can be made from a bioresorbable material. Examples of bioresorbable materials include poly-l-lactic acid and poly-lactic-acid compounds In a still further embodiment of the above aspects, the bone anchoring device can be made from a bioactive material. Examples of suitable bioactive materials can include calcium phosphate compounds, hydroxyapatite compounds and tricalcium phosphate compounds.

In a yet still further embodiment of the above aspects, the bone anchoring device can be a screw, stud, nail, rivet, dart, expanding coupling and anchor type device. A means of affixing the first end of the bone anchoring device with a bone can be a thread, a wedge, an expanding mechanism, a barb, a flange, a spline or other anchoring mechanism.

In still yet another embodiment of the first, third and fourth aspects, the bone anchoring device can have an attachment means for attachment to a thread or suture means positioned at or adjacent the second end of the bone anchoring device. The attachment means can provide sliding or permanent attachment with the thread means. Examples of an attachment means include an eyelet, clip, clamp, slot, groove or aperture.

In a first embodiment of the third and fourth aspects, the settable compound preferably has characteristics such that it can conform substantially to the surface of a bone prior to setting.

In a second embodiment of the third and fourth aspects, the settable compound can be bioresorbable, bioactive or bioactive and bioresobable. Suitable materials to be used as the settable material include calcium phosphorous sulphates and poly-l-lactic acid compounds.

In another embodiment of the third and fourth aspects, the settable compound has a setting time appropriate for surgical applications and bone fixation.

In a further embodiment of the third and fourth aspects, the settable compound has mechanical properties suitable for surgical applications and bone fixation. The settable compound can be reinforced or strengthened as required my reinforcement means. Examples of reinforcement means include particles, mesh and fibres.

In still a further embodiment of the third and fourth aspects, the settable compound can contain a medicament for therapeutic treatment of a subject. Examples of treatment can include direct treatment and prophylactic treatment.

In still yet a further embodiment of the third and fourth aspects, the fixation of bone can include fracture fixation, fixation of augmentation materials to bone, fixation of bone graft or graft-type material or stabilisation of distracted or displaced bone.

In a preferred embodiment of the third and fourth aspects, the present invention is used in the fixation of fractures of the cranium.

In a further preferred embodiment of the third and fourth aspects, plurality of bone anchoring devices can be used to fix a fractured cranium. The fracture can be a multiple fracture. The bone anchoring devices are affixed to the bone at sites appropriately located for fixation of the fracture.

In still a further preferred embodiment of the third and the fourth aspects, the fracture can be reduced manually, with instruments, with a thread or suture material passing through the apertures of the anchoring devices or combination of reduction methods.

In a still more preferable embodiment of the third and the fourth aspects, the thread is a bio-resorbable or bio-dissolvable suture material. The suture material can be secured to the apertures of the bone anchoring devices or be continuous through the apertures such that when tightened, the suture material providing initial stability and fixation of the fractured cranium. The suture material can connect between any two or bone anchoring devices depending upon the location of the fracture and the fixation required to stabilise the fracture.

Additional anchors and suture material can be introduced at any point throughout the procedure if required. Bone substitute, graft or augmentation material can be introduced into the fracture site for further stability. Therapeutic agents can also be introduced into or around the fracture site. The settable material is introduced such that it extends between any two or more bone anchoring devices and engages with the engagement means of the bone anchoring devices, and conforms to the geometry of the surface of the bone. The settable compound can at least partially cover the suture material.

BRIEF DESCRIPTION OF THE FIGURES

By way of example only, preferred embodiments of the invention are now described with reference to the accompanying drawings, in which.

DETAILED DESCRIPTION OF THE DRAWINGS

Figure 1:
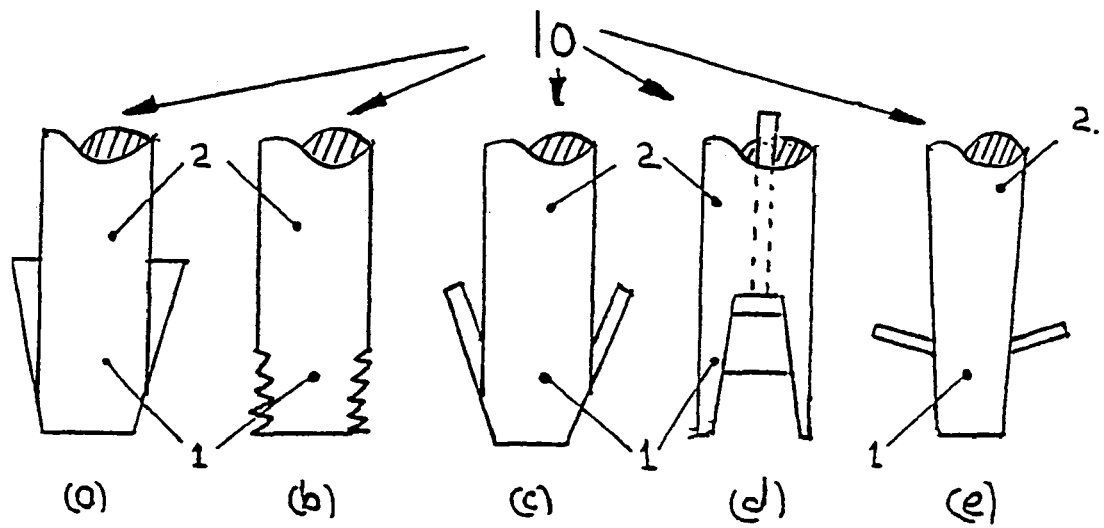
FIG. 1 depicts examples of means of affixing the bone anchoring device.

FIG. 1 depicts examples of affixment means at the first end 1 of the bone anchoring device 10. Shown in FIGS. 1(a), (b), (c), (d) and (e) are flange, screw, spline, expandable wedge and barb means respectively.

Figure 2:
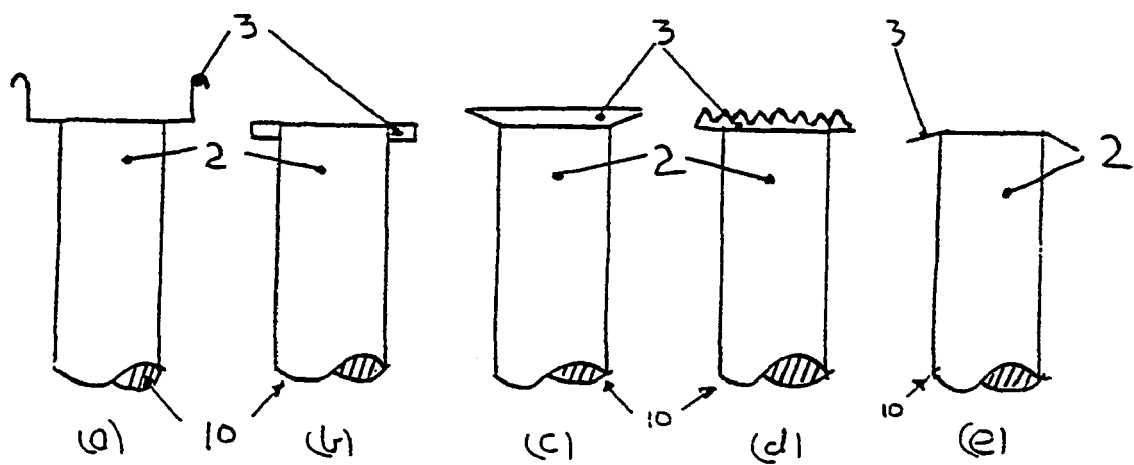
FIG. 2 depicts examples of engagement means of the bone anchoring device to engage with the settable compound.

FIG. 2 depicts examples of engagement means at the second end 2, of the bone anchoring device 10. Shown in FIGS. 2 (a), (b), (c), (d) and (e) are cusp, lip, flange, contour and pedestal engagement means respectively.

Figure 3:
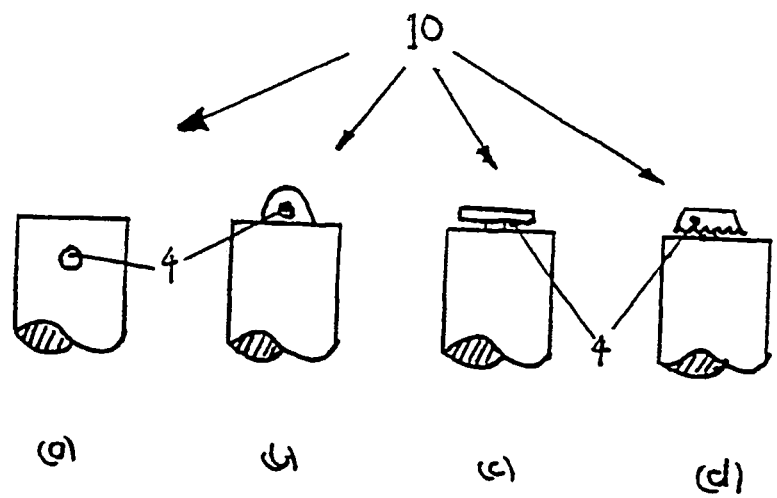
FIG. 3 depicts examples of attachment means for attaching a thread means to the bone anchoring device.

FIG. 3 depicts examples of attachment means 4 for attaching a thread material to the bone anchoring device 10. Shown in FIGS. 3 (a), (b), (c) and (d) are aperture, eyelet, boss and clamp attachment means respectively.

Figure 4:
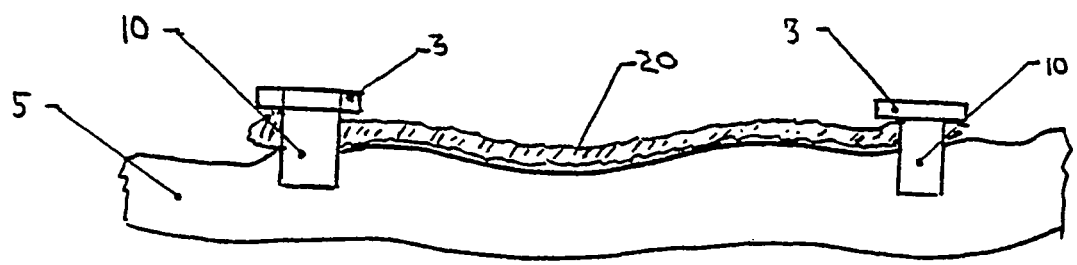
FIG. 4 depicts the bone anchoring means affixed to bone and engaged with the settable compound.

FIG. 4 depicts an example of two bone engagement means, 10, affixed to a bone 5, a settable compound 20 engaged with the engagement means 3 of the bone anchoring devices 10 and conforming substantially to the geometry and contour of the bone 5.

Figure 5:
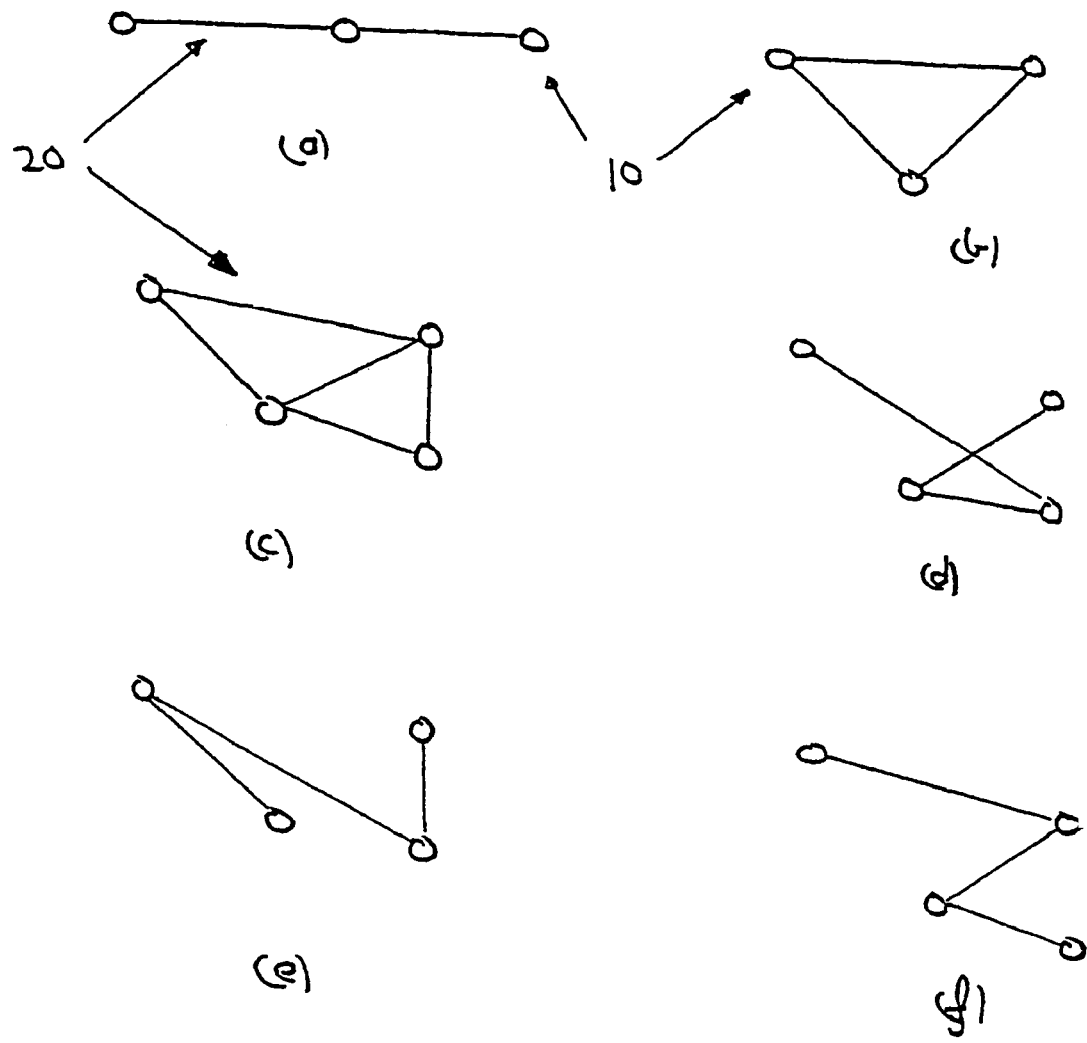
FIG. 5 depicts examples of configurations of bone anchoring anchoring means and settable compound.

FIG. 5 depicts examples of various configurations of bone engagement devices 10, linked and engaged with settable compound 20. As shown in FIGS. 5 (a), (b), (c) and (d), for the same arrangement of bone anchoring devices, several combination of arrangement of settable compound 20 is possible.

Figure 6:
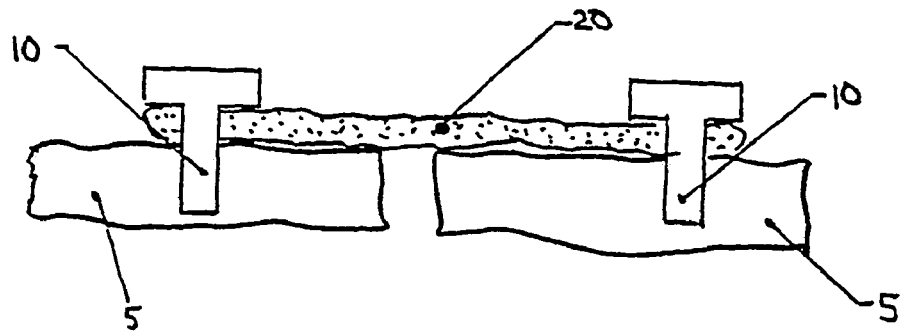
FIG. 6 depicts a bone fracture fixed in a distracted state by the bone engagement means and settable compound.

FIG. 6 depicts an example of a fractured bone 5 being held in a distracted configuration by a bone anchoring device 10 affixed to the bone 5 either side of the fracture and engaged with a settable compound. On setting, the settable compound 20 is engaged with each of the bone engagement means 10, effectively holding the fractured bone 5 apart in a distracted state. The settable compound is preferably bio-compatible and bio-resorbable. Examples of such a suitable material include calcium phosphorous sulphates and poly-l-lactic acid compounds.

Figure 7:
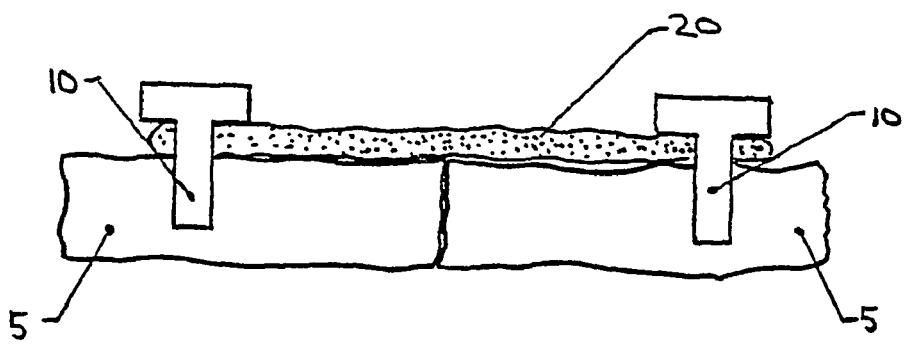
FIG. 7 depicts a bone fracture fixed in a reduced state by bone anchoring means and settable compound.

FIG. 7 depicts an example of a fractured bone 5 in a reduced state. The fracture can be reduced manually, by use of instruments, or a combination thereof. A bone anchoring device 10 is affixed to the bone each side of the fracture site. A settable compound 20 is applied to the surface of the bone 5, across the fracture site, substantially conforming to the geometry of the surface of the bone 5. The settable compound 20, when applied to the surface of the bone, also engages with the engagement means of each of the bone anchoring devices. Upon setting, the combination of the bone anchoring devices 10 and the cured settable compound 20 provide rigid fixation of the bone in a reduced state.

Figure 8:
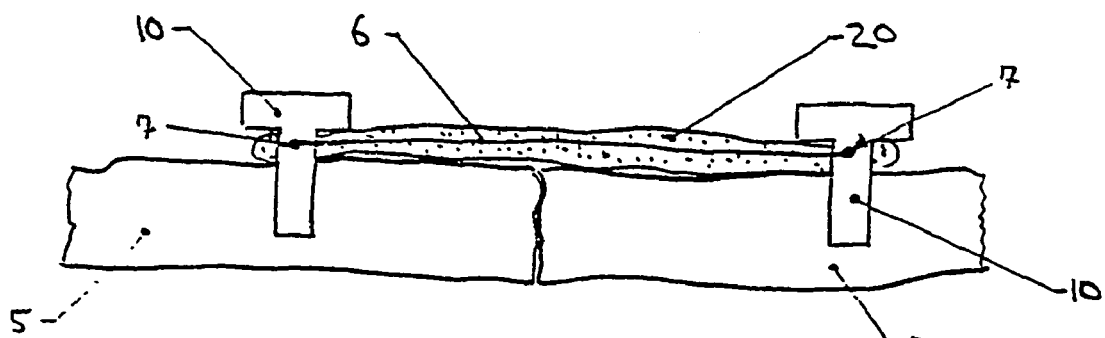
FIG. 8 depicts a bone reduced by a thread material and fixed in a reduced state by bone anchoring means and settable compound.

FIG. 8, as in FIG. 7, allows fixation of the fractured bone 5 in a reduced state. In FIG. 8, an aperture through the bone anchoring devices 10 allow a thread means 6, preferably a bio-resorbable suture material, to be used to hold the bone 5 in a reduced state prior to application of the settable compound 20. The fracture can be reduced manually, with instruments, by tightening the thread means 6, or a combination of reduction techniques. Once in a reduced state, the thread means 6 can be tied so as to secure the bone. The settable compound can be applied to such that it substantially conforms to the geometry of the surface of the bone 5, bridging and engaging with the bone anchoring devices 10, and may cover the thread means 6.

Upon setting, the settable material 20 in combination with the bone anchoring devices 10 maintains the fracture in a reduced state. It must be appreciated that in the event of more that two bone anchoring devices 10. and/or two fractures, the steps described above including the affixing of the bone anchoring devices 10, reducing the fracture and applying the settable compound can be performed in different orders depending on the nature of the fracture, the surgical site and requirement of the reduction procedure.

Figure 9:
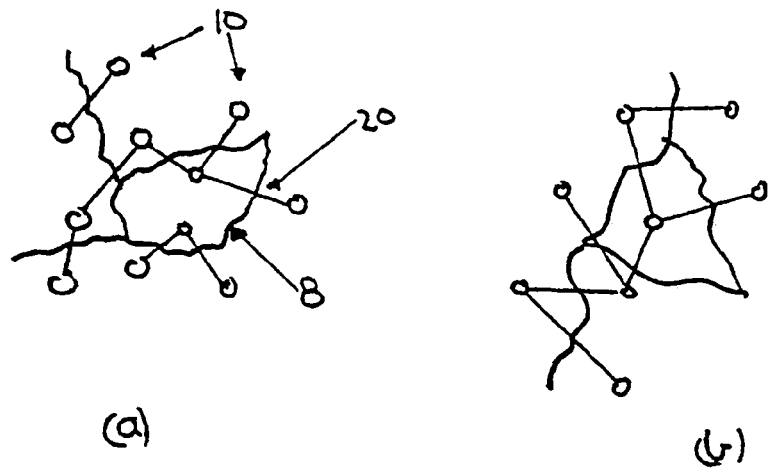
FIG. 9 depicts examples of a plurality of bone anchoring devices and settable compound used in fixation of a plurality of fractures.

FIG. 9 depicts two example of multiple fractures fixed using a plurality of bone anchoring devices 10 and a plurality of applications of settable compound 20. Depending on the nature, geometry physical anatomical requirement, the bone anchoring devices may need to be affixed to the fractured bone in a non-uniform distribution. Bridging between two or more bone anchoring devices 10 with settable compound 20 may be required depending upon the surgical requirements.

Figure 10:
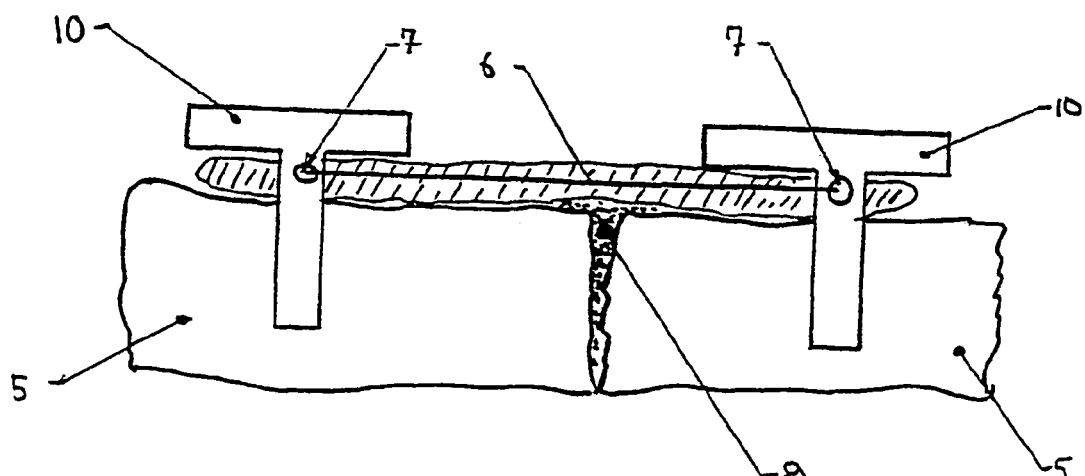
FIG. 10 depicts a bone fracture reduced by a thread device, augmented with therapeutic or bioactive substance and fixed in a reduced state by bone anchoring devices and settable compound.

FIG. 10, as in FIG. 8, depicts a reduced fracture fixed with two bone engagement devices and settable compound 20 bridging between the two bone anchoring devices 10 and engaging with the two bone anchoring devices 10. The fracture site is augmented with bone substitute or bone growth stimulating material 8. The fracture site can also be treated with a medicament It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A bone anchoring device, the device comprising:
   a first body and at least a second body, the first body and the second body each having:
   a first end affixable with a different separate piece of bone;
   engagement means defined by a second end opposite to the first end, said second end having multi-faceted projections engageable with the settable compound, and
   a settable compound conforming to a natural geometry of a surface of the different separate pieces of bone; and
   a flexible linking resorbable or permanent linking structure and the settable compound connecting the first body and the at least second body and extending therebetween to hold a relative positioning of the different separate pieces of bone in a reduced or distracted state.

2. The bone anchoring device according to claim 1, wherein the bone anchoring device further comprises a thread or suture attachment means positioned at or adjacent to a second end of the first body and the at least second body, for attachment to the thread, suture or wire, wherein the thread or suture attachment means provide sliding or permanent attachment with the thread or suture and comprises an eyelet, clip, clamp, slot, groove or aperture.

3. The bone anchoring device according to claim 2, wherein the engagement means is positioned at or adjacent the second end and is selected from the group comprising a cusp, flange, contour, lip, pedestal, coupling, and boss.

4. The bone anchoring device according to claim 1, wherein the first body and the at least second body are formed from a biocompatible material.

5. The bone anchoring device according to claim 1, wherein the settable compound is formed from a bioresorbable material.

6. The bone anchoring device according to claim 1, wherein the first body and the at least second body are formed from a bioactive material;
   wherein the bioactive material is formed from compounds selected from the group comprising calcium phosphate compounds, hydroxyapatite compounds and tricalcium phosphate compounds.

7. The bone anchor device according to claim 1, wherein the first body and the at least second body are selected from the group comprising a screw, stud, nail, rivet, dart, expanding coupling device, and anchor device.

8. The bone anchoring device according to claim 7, further comprising affixing means for affixing the first end of the first body and the at least second body with a bone, said affixing means is selected from the group comprising a screw thread, a wedge, an expanding mechanism, a barb, a flange and a spline.

9. The settable compound according to claim 1, wherein the settable compound is bioresorbable, bioactive, or bioactive and bioresobable.

10. The settable compound according to claim 9, wherein the settable compound is formed from calcium phosphorous sulphate or poly-l-lactic acid compounds.

11. The settable compound according to claim 1, wherein the settable compound has a setting time appropriate for surgical applications and bone fixation.

12. The settable compound according to claim 1, wherein the settable compound has mechanical properties suitable for surgical applications and bone fixation.

13. The settable compound according to claim 1, wherein the settable compound contains a medicament for therapeutic treatment of a subject.

14. A kit used in bone fixation, the kit comprising:
   a first bone anchoring device and at least a second bone anchoring device each having a first end affixble with a different separate piece of bone and engagement means for engaging with a settable compound,
   a flexible linking resorbable or permanent linking structure, brought into contact with the first bone anchoring device and the at least a second bone anchoring device and extending therebetween to hold a relative position of the different separate pieces of bone in a reduced or distracted state; and
   a settable compound extending between and connecting with the first and the at least second bone anchoring devices which are located on different separate pieces of bone at the time of implantation.

15. A method of bone fixation, the method including the steps of:
   (i) affixing a first bone anchoring device to a piece of a bone;
   (ii) affixing at least a second bone anchoring device to another separate piece of a bone;
   (iii) bringing a flexible linking resorbable or permanent linking structure into contact with the first bone anchoring device and the at least second bone anchoring device and maintaining a relative fixed position of the piece of bone to said another separate piece of bone; and
   (iv) applying a settable compound such that the settable compound conforms substantially to a natural geometry of the surface of the piece of bone and said another separate piece of bone, the settable compound extending from the first bone anchoring device to the at least a second bone anchoring device, such that upon setting, the settable compound engages with the bone anchoring devices;
   wherein the first and at least second bone anchoring device include a body having:
   a first end affixable with the piece of bone and said another separate piece of bone, respectively; and engagement means for engaging with the settable compound, attachment means provide sliding or permanent attachment with the thread or suture and comprises an eyelet, clip, clamp, slot, groove or aperture.

16. The method according to claim 15, wherein the method is used for the fixation of bone including fracture fixation, fixation of augmentation materials to bone, fixation of bone graft or graft-type material or stabilization of distracted or displaced bone.

17. The method according to claim 15, wherein the method is used for the fixation of fractures of the cranium, including multiple fractures.

18. The method according to claim 15, wherein the linking structure is a bio-resorbable or bio-dissolvable suture material.

19. The method according to claim 18, wherein additional bone anchoring devices and linking structure is introduced at any point throughout the procedure.

20. The method according to claim 19, wherein bone substitute, graft or augmentation material and/or a therapeutic agent is introduced into the fracture site for further stability.

* * * * *